United States Patent [19]
Lange et al.

[11] Patent Number: 5,274,167
[45] Date of Patent: Dec. 28, 1993

[54] POLYMERIABLE OPTICALLY ACTIVE (METH) ACRYLIC ACID DERIVATIVES

[75] Inventors: Walter Lange, Cologne; Bruno Bomer, Bergisch-Gladbach; Rolf Grosser, Leverkusen; Dieter Arlt, Cologne, all of Fed. Rep. of Germany

[73] Assignee: Bayer Aktiengesellschaft, Leverkusen, Fed. Rep. of Germany

[21] Appl. No.: 835,169

[22] Filed: Feb. 13, 1992

Related U.S. Application Data

[63] Continuation-in-part of Ser. No. 467,111, Jan. 18, 1990.

[30] Foreign Application Priority Data

Jan. 26, 1989 [DE] Fed. Rep. of Germany ....... 3902287
Jan. 26, 1989 [JP] Japan .................... 1-11972

[51] Int. Cl.$^5$ .............................. C07C 229/00
[52] U.S. Cl. ......................... 560/40; 526/304;
526/305; 526/306; 540/531; 546/243; 560/41;
560/159; 560/170; 564/159; 564/197; 564/199
[58] Field of Search ............. 526/304, 305, 306;
560/170, 40, 41, 159; 564/197, 159, 199;
546/243

[56] References Cited

U.S. PATENT DOCUMENTS

| | | | |
|---|---|---|---|
| 4,473,690 | 9/1984 | Yuki et al. | 526/265 |
| 4,914,159 | 4/1990 | Bömer et al. | 525/328.2 |
| 4,931,525 | 6/1990 | Schwartz et al. | 526/305 |

OTHER PUBLICATIONS

Lange et al.; CA 114 20, 1990.
Kuropka, et al; CA 112, 23, 1989.
El-Baba et al., CA 107, 11, 1986.
Matsunaga et al.; CA 105, 18, 1986.
Schomburg et al., CA 104, 14, 1985.
Ritter et al., CA 103, 18, 1985.
Rolf Kuropka, *Journal of Chromatography*, 1989, pp. 380-381.
G. Schomburg, *Journal of High Resolution Chromatography & Chromatography Communications*, 1985, pp. 391-394.
Helmut Ritter, *Makromol. Chem., Rapid Commun.*, 1985, pp. 521-525.
S. El-Baba et al, "Asymmetric Homogeneous Reduction of Dehydropeptides", pp. 3851-3855, vol. 42, No. 14, 1986.
74–Radiation Chem, Photochem., vol. 105, 1986, pp. 613-614 "Chemical Abstracts".
88:197559k, H. Batz et al, "Pharmacologically active polymers", Chem. Abstr., vol. 88, No. 26, Jun. 1978, p. 399.
105:162149u, S. Matsuga et al, "Silver halide color photographic material," Chem. Abstr., vol. 105, No. 18, Nov. 1986, p. 613.
105:66353k, K. Ulrich et al, "Polyethylene glycols containing enzymatically...," Chem. Abstr., vol. 105, No. 8, Aug. 1986, p. 369.

*Primary Examiner*—Paul R. Michl
*Assistant Examiner*—U. K. Rajguru
*Attorney, Agent, or Firm*—Sprung Horn Kramer & Woods

[57] ABSTRACT

An optically active N-(meth)acryloyl amino acid amide of the formula

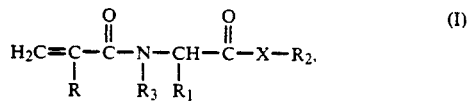

in which
R is hydrogen or methyl,
$R_1$ represents an optionally substituted alkyl, cycloalkyl, aralkyl, aryl or heteroaryl radical,
$R_3$ represents hydrogen or denotes together with $R_1$ a tri- or tetramethylene group;
X denotes oxygen or a $NR_4$-group wherein $R_4$ represents hydrogen or alkyl or denotes together with $R_2$ and the nitrogen atom a 5- to 7-membered ring which ring is optionally substituted by the group COO-alkyl (1-6 carbon atoms) or by one or two alkyl radicals (1-4 carbon atoms) and
$R_2$ denotes a strongly space-filling hydrocarbon radical.

The amide is polymerized and optionally bound to a support such as silica, and can then be used for the chromatographic separation of racemic mixtures of pharmacologically active compounds.

11 Claims, No Drawings

POLYMERIABLE OPTICALLY ACTIVE (METH) ACRYLIC ACID DERIVATIVES

This is a continuation-in-part of application Ser. No. 467,111, filed Jan. 18, 1990, now pending.

The invention relates to new optically active (meth)acrylic acid derivatives, to a process for their preparation, to their polymerization to give optically active polymers and to the use of these optically active polymers as adsorbents for the chromatographic separation of racemates into their enantiomers.

The separation of racemates into their optically active components has recently gained great importance since it has been established that the optical antipodes of biologically active racemates differ substantially in their biological activity and can have different effects and side effects. Great interest therefore exists in the isolation of the individual enantiomers of biologically active racemates.

All sorts of adsorbents have already been proposed for the chromatographic separation of racemates; hitherto the optimum adsorbents here have proved to be the polymeric (meth)acrylic acid derivatives of optically active amino compounds described in Chem. Ber. 109 (1976), 1967-1975, DE-A-2,500,523, 3,532,356, 3,619,303 and 3,706,890, if appropriate in silica gel-bound form.

However, when using the known polymeric (meth)acrylic acid derivatives of optically active amino compounds, it has been shown that these either have only an insufficient effect, this is, for example, the case in the polymers of N-(meth)acryloyl amino acid esters described in Chem. Ber. 109 loc. cit. and in DE-A-3,619,303 and the polymers of (meth)acrylamides described in DE-A-2,500,523, or they have a good activity which, however, is only limited to certain racemates, this is, for example, the case with the polymers of the optically active poly(meth)acrylamides described in DE-A-3,532,356 and 3,706,890, which are derived from optically active N-(meth)acryloyl-terpenylamines.

It has now been found that adsorbents having substantially improved separating properties are obtained by polymerizing optically active N-(meth)acryloyl amino acid esters and amides, whose conformation is so restricted as a result of the steric requirement of the ester or amide group in the optically active amino acid esters or amides, optionally assisted by the methyl group of the methacryloyl radicals that the molecule of the optically active N-(meth)acryloyl amino acid derivative is totally rigid. It has been found that the strongly improved separating properties always occur if the ester or amide groups of the optically active amino acid derivative contain a bulky, i.e. space-filling, hydrocarbon radical. It has been found that the space-filling of the tert.-butyl group alone is insufficient, and that it is only sufficient, for a determination of the conformation of the N-(meth)acryloyl amino acid tert.-butyl ester or amide in combination with the N-methacryloyl radical, while large-volume alkyl radicals, such as the neopentyl radical or the various terpenyl radicals alone already determine the conformation sufficiently, independently of whether the amino group of the optically active amino acid derivative is bonded to an acryloyl or methacrylayl radical.

The rigidity of the molecule of the optically active N-(meth)acryloyl amino acid derivative leads to a substantial improvement in the separating properties of the polymers prepared from these optically active amino acid derivatives.

Of the separating materials according to the inventions for example, even tetra- and hexahydrocarbazole and also hydroxyalkylazole derivatives, which cannot be resolved or can only be resolved very unsatisfactorily into the enantiomers on the known phases, can be well separated.

The invention therefore relates to optically active N-(meth)acryloyl amino acid derivatives of the formula (I)

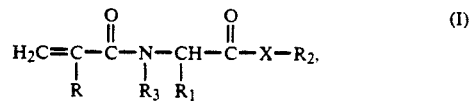

in which

R is hydrogen or methyl, $R_1$ represents an optionally substituted alkyl, cycloalkyl, aralkyl, aryl or heteroaryl radical, $R_3$ represents hydrogen or denotes together with $R_1$ a tri- or tetramethylene group, X denotes oxygen or a $NR_4$-group wherein $R_4$ represents hydrogen or alkyl or denotes together with $R_2$ and the nitrogen atom a 5- to 7-membered ring which ring is optionally substituted by the group COO-alkyl (1-6 carbon atoms) or one or two alkyl radicals (1-4 carbon atoms), and $R_2$ denotes a strongly space-filling hydrocarbon radical, for example a tertiary alkyl radical, an optionally substituted cycloalkyl, aryl or heteroaryl radical or a terpenyl or adamantyl radical, with the proviso that if $R_2$ is a tertiary butyl group, R must be a methyl group.

Preferred compounds of formula (I) are those in which

R is hydrogen or methyl, $R_1$ represents alkyl with 1 to 18 carbon atoms or cycloalkyl with 3 to 8 carbon atoms which are optionally substituted by hydroxy, halogen, alkyl, alkoxy or cycloalkyl with up to 8 carbon atoms or by an aryl group with 4 to 14 carbon atoms which optionally contain 1 or 2 hetero atoms from the group nitrogen, oxygen and/or sulfur wherein these aryl- and heteroaryl groups are optionally substituted by hydroxy, halogen, alkyl or alkoxy with 1 to 4 carbon atoms, or represents an aryl- or heteroaryl group with 4 to 14 carbon atoms which may contain 1 or 2 identical or different hetero atoms from the group nitrogen, oxygen or sulfur and which are optionally substituted by hydroxy, halogen$ alkyl or alkoxy with 1 to 4 carbon atoms each, $R_3$ represents hydrogen or denotes together with $R_1$ a tri- or tetramethylene group, X denotes oxygen or the group $NR_4$ wherein $R_4$ represents hydrogen or alkyl with 1 to 4 carbon atoms or $R_4$ builds together with $R_2$ and the nitrogen atom a 5- to 7-membered heterocyclic ring which ring may optionally be substituted by the group COO-alkyl (1-4 carbon atoms) or one or two alkyl radicals (1-4 carbon atoms), and $R_2$ denotes a strongly space-filling hydrocarbon radical with up to 30 carbon atoms selected from the group tert.-alkyl with 4 to 20 carbon atoms, $CH_2$-tert.-alkyl with 4 to 20 carbon atoms, cycloalkyl with 3 to 10 carbon atoms, aryl with 4 to 14 carbon atoms which may contain 1 or 2 identical or different hetero atoms from the group nitrogen, oxygen or sulfur, which forementioned alkyl-, cycloalkyl-, aryl- and heteroaryl-groups are optionally substituted by halogen, hydroxy, alkyl with 1 to 8 carbon atoms and/or alkoxy with I to 8 carbon atoms, or $R_2$ denotes terpenyl, adamantyl or decahydronaphthyl, with the proviso that if $R_2$ is a tertiary butyl group, R must be a methyl group.

All alkyl- and alkoxy groups mentioned herein are preferably those with 1 to 4 carbon atoms.

The following radicals may be mentioned as optionally substituted alkyl, cycloalkyl, aralkyl, aryl and heteroaryl radicals for $R_1$:

the methyl, ethyl, i-propyls n-propyl, n-butyl, i-butyl, sec.-butyl, tert.-butyl, 1-hydroxyethyl, 2-alkoxycarbonyl, 3-alkoxycarbonyl, 3-N-acylaminopropyl, 4-N-acylaminobutyl, tert.-butoxymethyl and the hydroxymethyl radical as optionally substituted alkyl radicals;

the cyclohexyl and the 2-tetrahydronaphthyl radical as optionally substituted cycloalkyl radicals;

the benzyl and 4-hydroxybenzyl radical as optionally substituted aralkyl radicals;

the phenyl and naphthyl radical as optionally substituted aryl radicals;

the 3-indolyl radical as an optionally substituted heteroaryl radical.

The following may be mentioned, for example, as strongly space-filling radicals for $R_2$:

tertiary alkyl radicals such as the tert.-butyl, the neopentyl and the adamantyl radical;

alkyl radicals substituted in the 1-position by cycloalkyl groups such as the cyclohexylmethyl or cyclapropylmethyl radical;

optionally substituted cycloalkyl radicals such as the cyclohexyl and the cyclohexyl radicals substituted by methyl or tert.-butyl groups such as the 2- or 3-methylcyclohexyl, 4-tert.-butyl and 2,6-di-tert.-butylcyclohexyl radical or decahydronaphthyl;

optionally substituted phenyl radicals such as the phenyl radical or phenyl radicals substituted by $C_1$-$C_4$-alkyl groups such as the o-talyl, 2,6-xylyl, 4-tert.-butyl and 2,6-di-tert.-butyl-phenyl radical; terpenyl radicals such as the menthyl, neomenthyl, bornyl, fenchyl and pinanyl radical.

The use of optically active radicals for $R_2$, for example the d- or l-1-phenylethyl or the d- or l-menthyl, d- or l-neomenthyl, d- or l-bornyl, d- or l-fenchyl or d- or l-pinanyl radical, is particularly advantageous.

The optically active N-(meth)acryloyl amino acid derivatives of the formula (I) according to the invention are preferably derived from optically active amino acids such as alanine, aminobutyric acid, valine, norvaline, leucine, isoleucine, terleucine, phenylglycine, phenylalanine, naphthylalanine, cyclohexylglycine, cyclohexylalanine, tyrosine, tryptophan, threonine, serine, aspartic acid, glutamic acid, ornithine, lysine or proline.

Preferred optically active N-(meth)acryloyl amino acid derivatives of the formula (I) according to the invention are the N-methacryloyl derivatives of the tert.-butyl esters of the following amino acids: alanine, valine, leucine, isoleucine, phenylglycine, cyclohexylglycine, phenylalanine, cyclohexylalanine, O-tert.-butylserine, N'-acyllysine, for example N'-t-butoxycarbonyllysine and N'-acylornithine; the N-(meth)acryloyl derivatives of the bornyl, menthyl and fenchyl esters of the following amino acids: alanine, phenylalanine, cyclohexylalanine, naphthylalanine, phenylglycine, cyclohexylglycine, leucine, isoleucine, valine, lysine, ornithine; the N-(meth)acryloyl derivatives of the 4-tert.-butylcyclohexyl esters of the following amino acids: alanine, phenylalanine, cyclohexylalanine, phenylglycine, cyclohexylglycine, naphthylalanine, leucine, isoleucine and valine;

the N-(meth)acryloyl derivatives of the 2-decahydronaphthyl esters of the following amino acids: alanine, valine, leucine, isoleucine, phenylglycine, cyclohexylglycine, phenylalanine, cyclahexylalanine and naphthylalanine;

the N-(meth)acryloyl derivatives of the menthyl 1-cyclohexylethyl and 1-phenylethylamides of the following amino acids: alanine, valine, leucine, isoleucine, phenylglycine, cyclohexylglycine, phenylalanine, cyclohexylalanine, naphthylalanine and proline.

Particularly preferred N-(meth)acrylayl amino acid derivatives of the formula (I) are: N-(meth)acryloylalanine menthyl ester, N-(meth)acryloylalanine bornyl ester, N-(meth)acryloylalanine fenchyl ester, N-(meth)acryloylphenylalanine menthyl ester, N-methacryloylphenylglycine tert.-butyl ester, N-methacrylaylleucine tert.-butyl ester, N-methacryloylphenylalanine tert.-butyl ester, N-(meth)acrylcylvaline trans-4-tert.-butylcyclohexyl ester and N-methacryloyl-N'-tert.-butoxycarbonyllysine tert.-butyl ester, N-methacryloylisoleucine tert.-butyl ester, N-methacryloylvaline tert.-butyl ester, N-methacryloylcyclchexylalanine tert.-butyl ester, N-(meth)acryloylalanine 2-decahydronaphthylester, N-(meth)acrylaylalanine menthyl amide, N-(meth)acryloylphenylalanine menthyl amide, N-(meth)acryloylphenylalanine 1-phenylethyl amide.

The optically active N-(meth)acryloyl amino acid derivatives of the formula (1) according to the invention are obtained by the reaction of optically active amino acid derivatives of the formula

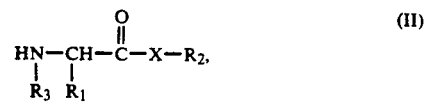

in which $R_1$ and $R_2$ have the meanings indicated under formula (I), or their acid addition products with (meth)acrylic acid derivatives of the formula

in which

Y represents a removable group and

R has the meaning indicated under formula (I), if appropriate in the presence of an acid-binding agent in inert organic solvents.

Removable groups which may be mentioned are: halogen atoms, in particular chlorine or bromine, or a group of the formula $OR_5$, in which $R_5$ represents a $C_1$-$C_4$-alkyl group or a $CH_2$=$C(R)$—COO group (in which R has the meaning indicated under formula (I)).

The reaction can be carried out at normal, elevated or reduced pressure. In general, the reaction is carried out at normal pressure.

The compounds of the formulae (II) and (III) are preferably employed in equimolar amounts.

The optically active amino acid esters of the formula (II) and the acrylic acid derivatives of the formula (III) used as starting compounds are known or can be prepared by methods which are known per se (see Bull. Chem. Soc. Jap. 37 (19), 191; EP-A-256,475; Beilsteins Handbuch der organischen Chemie (Beilstein's Handbook of Organic Chemistry), volume 2, 3rd supplement, page 1293; volume 2, original work, page 400).

Suitable acid addition compounds of the amino acids to be used as starting compounds are salts of these amino acids with inorganic or organic acids. Those preferred are mineral acids such as hydrochloric acid, hydrobromic acid, sulphuric acid, phosphoric acid or organic acids such as acetic acid, methanesulphonic acid, ethanesulphonic acid, benzenesulphonic acid or toluenesulphonic acid.

Suitable solvents are all organic solvents which are inert under the reaction conditions. Those preferred are hydrocarbons such as benzene, toluene, xylene or mineral oil fractions, or halogenated hydrocarbons such as di-, tri- or tetrachloromethane, dichloroethane or trichloroethylene.

Suitable acid-binding agents are in particular the customary inorganic or organic bases. Those preferably used are alkali metal hydroxides or alkaline earth metal hydroxides such as sodium hydroxide, potassium hydroxide, lithium hydroxide, calcium hydroxide or barium hydroxide, alkali metal or alkaline earth metal carbonates such as sodium carbonate or potassium carbonate, alkali metal alkoxides such as sodium methoxide, sodium ethoxide, potassium methoxide, potassium ethoxide or amines such as triethylamine or pyridine.

The reaction of the (meth)acrylic acid derivatives of the formula (III) with the amino acid derivatives of the formula (II) is carried out at temperatures from $-78°$ to $+100°$ C., preferably from $-10°$ C. to $+60°$ C.

The invention furthermore relates to the optically active poly(meth)acrylamides obtainable by polymerization of the optically active N-(meth)acryloyl amino acid derivatives of the formula (I), which contain structural units of the formula

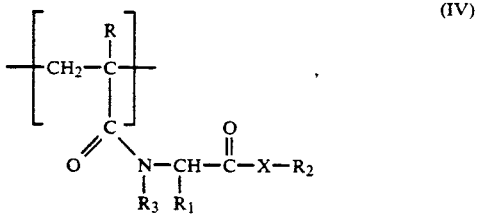

(IV)

in which R, $R_1$, $R_2$, $R_3$ and X have the meanings indicated under formula (I).

The optically active poly(meth)acrylamides according to the invention are preferably present in the form of cross-linked insoluble but swellable polymers or in a form bound to finely divided inorganic support materials. They can also be prepared as linear polymers soluble in suitable organic solvents. It is further possible to copolymerize different (meth)acrylamide monomers according to the invention and to incorporate 0.1 to 60, preferably 0.1 to 20, mol % of copolymerizable, non-chiral monomers into the polymer.

The cross-linked polymers are preferably present in the form of finely divided beads having a particle diameter of 5-200 μm. They are prepared in a manner known per se by suspension polymerization of the optically active (meth)acrylamide monomers of the formula (I) with 0.5-50 mol %, preferably 1-20 mol %, particularly preferably 3-15 mol % (relative to the total amount [mol] of the monomers employed) of a suitable cross-linker.

The degree of swelling of the (bead) polymers can be adjusted by the type and amount of the cross-linker (the cross-linkers).

In practical use, (bead) polymers having a degree of swelling (Q) of 1.1 to 10, preferably 2.0 to 7.0, have proved suitable, $$Q = \frac{\text{resin volume (swollen)}}{\text{resin volume (unswollen)}}$$

Possible cross-linking agents are compounds which contain at least two polymerizable vinyl groups. Preferred cross-linking agents are alkanediol diacrylates such as 1,6-hexanediol diacrylates 1,4-butanediol diacrylate, 1,3-propanediol diacrylate or 1,2-ethylene glycol diacrylate or alkanediol dimethacrylate such as 1,4-butanediol dimethacrylate, 1,3-propanediol dimethacrylate or 1,2-ethylene glycol dimethacrylate, aromatic divinyl compounds such as, for example, divinylbenzene, divinylchlorobenzene or divinyltoluene, alkanedicarboxylic acid vinyl esters such as divinyl adipates divinyl benzenedicarboxylate, divinyl terephthalate, N,N'-alkylenediacrylamides such as N,N'-methylenediacrylamide, N,N'-ethylenediacrylamide, N,N'-methylenedimethacrylamide or N,N'-ethylenedimethacrylemide.

Suitable radical formers are the customary radical formers. Those preferred are peroxides such as, for example, dibenzoyl peroxide, dilauroyl peroxide or diorthotolyl peroxide or azo compounds such as, for example, azobisisobutyronitrile (AIBN). Mixtures of different radical formers are also utilizable.

The polymerization components are dissolved in an organic solvent, preferably an aromatic hydrocarbon such as benzene or toluene, or a halogenated hydrocarbon such as di-, tri- or tetrachloromethane or 1,2-dichloroethane.

The organic phase is uniformly dispersed with the aid of an effective stirrer into the aqueous solution of a protective colloid, preferably into an aqueous solution of polyvinyl alcohol, polyvinylpyrrolidone or a copolymer of methacrylic acid and methyl methacrylate. About 1 to 20, preferably 2 to 10, parts by weight of aqueous phase are used per part by weight of organic phase. The polymerization mixture is heated with stirring in an inert gas atmosphere, preferably under nitrogen, to temperatures of 30° C. to 100° C., preferably 40° C. to 80° C. The duration of polymerization is between 2 and 24, preferably 4 and 12 hours. The copolymer obtained in this manner is separated from the liquid phase by filtration, purified by thorough washing with water and with organic solvents such as methanol, ethanol, benzene, toluenes di- or trichloromethane or acetone and then dried.

The preparation of the optically active poly(meth)acrylamides according to the invention in a form bound to inorganic support materials, preferably to silica gel, can be carried out, for example, according to the method described in DE-A-3,706,890.

The polymerization of the optically active (meth)acrylamides in the presence of silica gel-diol phases, which have been esterified with (meth)acrylic acid, is widely utilizable. In this case, the polymerization can be carried out in the absence of solvents or in the presence of solvents or precipitating agents for the poly(meth)acrylamides. The radical formers used for the preparation of bead polymers can likewise be employed as initiators.

The polymer-modified silica gels are intensively washed with solvents for the polymers and dried in vacuo.

The invention further relates to the use of the poly(meth)acrylamides according to the invention as such or in crosslinked or silica gel-bound form for the chromatographic separation of racemic mixtures into the optical antipodes. The polymers according to the invention have proved particularly suitable for the chromatographic separation of tetrahydro- or hexahydrocarbazole derivatives such as, for example, 3-(4-chlorophenylsulphonamido)-9-(2-carboxyethyl)-1,2,3,4-tetrahydrocarbazole, 3-r-(benzenesulphonamido)-9-(2-carboxyethyl)-1,2,3,4,4a,9a-hexahydrocarbazole, 1-(carboxymethyl)-6-fluoro-9-(4-chlorobenzyl)-1,2,3,4-tetrahydrocarbazole, hydroxyalkylazole derivatives such as, for example, 2-(4-chloraphenyl)-3-methoxyimino-3-methyl-1-(1-(1,2,3-triazolyl)-2-butanol and erythro-1-(4-chlorophenoxy)-1-(1-(1,2,4-triazolyl))-3,3-dimethyl-2-butanol and also lactone derivatives such as, (E)-6α-[2-[3-(4-fluorophenyl)-1-(1-methylethyl)-1H-indol-2-yl]-ethenyl]tetrahydro-4β-hydroxy-2H-pyran-2-one, (E)-6α-[2-(3,5-dichloro-4'-fluoro-[1,1'-biphenyl]-2-yl)-ethenyl]tetrahydro-4β-hydroxy-2H-pyran-2-one and 2-(4-isobutylphenyl)-propionic acid.

The composition of the eluent can be selected and optimized in a customary manner depending on the type and properties of the racemate to be separated. The silica gel-bound poly(meth)acrylamide according to the invention can be employed for chromatographic racemate separations under HPLC conditions.

The ability of the polymers to separate racemates is expressed by the capacity ratios ($k'_{1(2)}$ values) for the two enantiomers (1) and (2) and the enantioselectivity value α resulting therefrom. These chromatographic parameters are defined as follows:

$$\text{capacity ratio } k'_{1(2)} = \frac{t_{1(2)} - t_o}{t_o}$$

$$\text{Enantioselectivity } \alpha = \frac{k'_2}{k'_1}$$

$t_o$ = dead time of the column
$t_{1(2)}$ = retention time of the initially eluted enantiomer 1 or the subsequently eluted enantiomer 2

The preparative separation of racemic mixtures into their optical antipodes using the polymers according to the invention is preferably carried out by column chromatography, It is particularly advantageous for this purpose to perform the chromatographic separation using bead polymers of a certain particle size distribution; good separating efficiencies were obtained with bead polymers of a particle size distribution from 5–200 μm, preferably 15–100 μm.

The working methodology of separation by column chromatography is known. The polymer is customarily suspended in the eluent and the suspension is packed into a glass column. After running off the eluent, the racemate to be separated, dissolved in as little eluent as possible, is applied to the column. The latter is then eluted with eluent and the enantiomers are detected in the eluate photometrically and/or polarimetrically by means of suitable flowthrough cells.

Customary organic solvents or solvent mixtures which swell the polymer employed as the adsorbent and dissolve the racemate to be separated are used as eluents. Examples which may be mentioned are: hydrocarbons such as benzene, toluene or xylene, ethers such as diethyl ether, dioxane or tetrahydrofuran, halogenated hydrocarbons such as di- or trichloromethane, acetone, acetonitrile or ethyl acetate or else mixtures of the solvents mentioned. Mixtures of toluene and tetrahydrofuran and of toluene and dioxane have proved particularly suitable.

EXAMPLES

Preparation of the optically active N-(meth)acryloyl amino acid derivatives

EXAMPLE 1

39.4 g (0.39 mol) of triethylamine are added dropwise at 0° C. to a solution of 49.3 g (0.187 mol) of D-alanine l-menthyl ester hydrochloride in 750 ml of dichloromethane, then a solution of 17.2 g (0.19 mol) of acryloyl chloride in 50 ml of dichloromethane is added dropwise at −10° C. The reaction mixture is stirred at room temperature for 12 hours and then washed with water, 5% strength hydrochloric acid and saturated sodium hydrogencarbonate solution. The organic phase is dried over magnesium sulphate. After distilling off the solvent, the residue is recrystallized from petroleum ether.

35.4 g of N-acryloyl-D-alanine l-menthyl ester are obtained in the form of colorless crystals of m.p. 79° C.
Rotation $[\alpha]_D$: −67.0° (c=1, CHCl$_3$)

The residue can also be purified by chromatography on silica gel using aft ether/petroleum ether 1:1 mixture as the eluent instead of by crystallization.

Instead of the D-alanine l-menthyl ester hydrochloride, the free amino ester can also be employed to the same effect.

The amount of triethylamine can then be reduced to 0.19 mol.

From the optically active amino acid derivatives indicated in Tables I and Ia, the optically active N-(meth)acryloyl amino acid derivates also indicated in Table I and Ia were obtained in the manner described above for the preparation of the N-acryloyl-D-alanine l-menthyl ester. The yields, the melting points and the rotations of the amino acid derivatives obtained are also indicated in the tables.

TABLE I

| Example | Optically active amino acid derivative used | N-(meth)acryloyl amino acid derivative obtained | m.p.[°C.] | $[\alpha]_D$ (C = 1, CHCl$_3$) | Yield (% of theory) |
|---|---|---|---|---|---|
| 2 | L-alanine d-menthyl ester | N-A-L-alanine d-methyl ester | 79 | +67.2 | 70 |
| 3 | L-alanine l-menthyl ester | N-A-L-alanine l-methyl ester | 64 | −56.1 | 84 |
| 4 | D-aminobutyric l-menthyl ester | N-A-D-aminobutyric l-menthyl ester | 72 | −64.2 | 78 |
| 5 | L-valine l-menthyl ester | N-A-L-valine l-menthyl ester | 78 | +65.7 | 77 |
| 6 | D-valine l-menthyl ester | N-A-D-valine l-menthyl ester | 72 | −58.4 | 80 |

TABLE I-continued

| Example | Optically active amino acid derivative used | N-(meth)acryloyl amino acid derivative obtained | m.p.[°C.] | $[\alpha]_D$ (C = 1, CHCl$_3$) | Yield (% of theory) |
|---|---|---|---|---|---|
| 7 | L-norvaline d-menthyl ester | N-A-L-norvaline d-menthyl ester | 54–55 | +70.7 | 67 |
| 8 | L-leucine l-menthyl ester | N-A-L-leucine l-menthyl ester | 72 | −18.0 | 90 |
| 9 | L-leucine d-menthyl ester | N-A-L-leucine d-menthyl ester | 79 | +35.0 | 87 |
| 10 | D-phenylglycine l-menthyl ester | N-A-D-phenylglycine l-menthyl ester | 130 | −176.5 | 75 |
| 11 | D-phenylglycine d-menthyl ester | N-A-D-phenylglycine d-menthyl ester | 126 | +148.2 | 88 |
| 12 | L-phenylalanine d-menthyl ester | N-A-L-phenylalanine d-menthyl ester | 79 | +97 | 78 |
| 13 | L-alanine d-menthyl ester | N-Mea-L-alanine d-menthyl ester | 58 | +68.9 | 92 |
| 14 | L-alanine (+)-fenchyl ester | N-A-L-alanine (+)-fenchyl ester | Oil | +29.6 | 84 |
| 15 | L-phenylalanine l-menthyl ester | N-A-L-phenylalanine l-menthyl ester | 118 | −117.4 | 77 |
| 16 | L-glutamic di-l-menthyl ester | N-A-L-glutamic di-l-menthyl ester | Oil | +78.1 | 60 |
| 17 | L-valine l-menthylamide | N-A-L valine l-menthylamide | 214 | +15.4 | 72 |
| 18 | L-leucine tert.-butyl ester | N-Mea-L-leucine tert.-butyl ester | 78 | +37.7 | 86 |
| 19 | D-phenylglycine tert.-butyl ester | N-Mea-D-phenylglycine tert.-butyl ester | 118 | −125.0 | 74 |
| 20 | L-phenylalanine tert.-butyl ester | N-Mea-L-phenylalanine tert.-butyl ester | 67 | +64.7 | 75 |
| 21 | N-ε-tert.-butoxycarbonyl-L-lysine tert.-butyl ester | α-N-Mea-N-ε-tert.-butoxy carbonyl-L-lysine tert.-butyl ester | 71 | +21.1 | 76 |
| 22 | D-phenylglycine cyclohexyl ester | N-Mea-D-phenylglycine cyclohexyl ester | 62 | −85.9 | 85 |
| 23 | L-isoleucine tert.-butyl ester | N-Mea-L-isoleucine tert.-butyl ester | 63 | +52.6 | 84 |
| 24 | L-leucine cyclohexyl ester | N-Mea-L-leucine cyclohexyl ester | 83 | +2.1 | 79 |
| 25 | L-leucine cyclohexyl ester | N-A-L-leucine cyclohexyl ester | 105 | −3.9 | 74 |
| 26 | L-alanine l-bornyl ester | N-A-L-alanine l-bornyl ester | 88 | −31.6 | 78 |
| 27 | L-alanine d-menthylamide | N-A-L-alanine d-menthylamide | 200 | −8.5 | 70 |
| 28 | L-alanine 2-decahydro-naphthyl ester | N-A-L-alanine 2-decahydro-naphthyl ester | Oil | +2.2 | 77 |
| 29 | L-valine (trans-4-tert.-butylcyclohexyl) ester | N-A-L-valine (trans-4-tert.-butylcyclohexyl) ester | 79 | +2.7 | 66 |
| a | D-phenylglycine tert.-butyl ester | N-A-D-phenylglycine tert.-butyl ester | 110 | −190.8 | 81 |
| b | L-leucine tert.-butyl ester | N-A-L-leucine tert.-butyl ester | 70 | +5.75 | 85 |

N-A = N-acryloyl
N-Mea = N-methacryloyl

II. Polymerization of the N-(meth)acryloyl amino acid derivatives

1. Preparation in the form of bead polymers

The solution from 13.5 g of optically active N-(meth)acryloyl amino acid derivative, 1.5 g of ethylene glycol dimethacrylate and 0.3 g of azobisisobutyronitrile in 37.5 g of trichloromethane is dispersed with stirring (350 to 500 rpm) in a solution of 3 g of polyvinyl alcohol in 130 ml of demineralized water. The apparatus is evacuated and filled with nitrogen several times. The polymerization mixture is stirred under nitrogen, first for 30 minutes at room temperature and then for 16 hours at 55° C. (internal temperature). The polymerization mixture is then stirred into 2 to 3 l of water and the liquid phase is decanted after settling of the bead polymer. The bead polymer is freed from the fines (polymer having a particle size of <10 μm) by suspending in water 3 to 4 times and decanting off the liquid phase and, after intensive washing with acetone, is dried to constant weight at 60° C.

The N-(meth)acryloyl amino acid derivatives used for the polymerization, the rate of stirring at which the polymerization was carried out, the yields in which the polymers were obtained, their particle size and the volume of the bead polymer obtained in the dry ($V_s$) and swollen ($V_q$) state (swelling agent: toluene) are compiled in Tables II and IIa below:

TABLE II

| Example No. | N-(meth)acryloyl amino acid derivative as in Example | Rate of stirring [rpm] | Yield of beads > 10 μm [g] | Particle size of the beads [μm] | $V_s$ [ml/g] | $V_q$ [ml/g] |
|---|---|---|---|---|---|---|
| 30 | 1 | 350 | 9.5 | 10–50 | 2.4 | 4.7 |
| 31 | 2 | 550 | 11.7 | 20–100 | 2.0 | 5.2 |
| 32 | 3 | 350 | 10.6 | 20–100 | 1.9 | 4.0 |
| 33 | 4 | 500 | 12.2 | 20–100 | 1.7 | 4.9 |
| 34 | 5 | 400 | 9.9 | 20–80 | 1.6 | 3.9 |
| 35 | 6 | 450 | 9.7 | 20–80 | 2.3 | 6.9 |
| 36 | 7 | 350 | 9.8 | 40–130 | 1.4 | 5.2 |

TABLE II-continued

| Example No. | N-(meth)acryloyl amino acid derivative as in Example | Rate of stirring [rpm] | Yield of beads > 10 μm [g] | Particle size of the beads [μm] | $V_s$ [ml/g] | $V_q$ [ml/g] |
| --- | --- | --- | --- | --- | --- | --- |
| 37 | 9 | 400 | 9.2 | 20–70 | 1.6 | 6.6 |
| 38 | 10 | 500 | 12.1 | 20–70 | 2.2 | 6.3 |
| 39 | 12 | 400 | 12.4 | 20–90 | 2.2 | 5.3 |
| 40 | 13 | 500 | 10.2 | 20–90 | 2.2 | 6.8 |
| 41 | 14 | 450 | 10.7 | 20–70 | 1.9 | 5.6 |
| 42 | 15 | 350 | 10.7 | 15–50 | 2.2 | 6.8 |
| 43 | 16 | 450 | 11.0 | 20–100 | 1.8 | 5.8 |
| 44 | 18 | 400 | 12.1 | 20–120 | 1.6 | 6.5 |
| 45 | 19 | 400 | 10.6 | 20–90 | 2.0 | 4.9 |
| 46 | 20 | 450 | 12.2 | 15–80 | 1.6 | 4.6 |
| 47 | 21 | 500 | 11.3 | 15–70 | 1.8 | 3.8 |
| 48 | 22 | 450 | 12.0 | 15–60 | 1.6 | 4.5 |
| 49 | 26 | 450 | 11.4 | 20–100 | 1.7 | 6.0 |
| a | I a | 400 | 10.6 | 20–90 | 2.0 | 4.9 |
| b | I b | 400 | 9.8 | 20–80 | 1.6 | 4.2 |

2. Preparation in silica gel-bound form a) 25 g of silica gel modified with 1,2-diol groups (average particle size: 5 μm) are suspended in 500 ml of dioxane under nitrogen with the exclusion of moisture. 16 ml of methacrylic anhydride and 12.5 ml of triethylamine are added to the suspension. The mixture is stirred for 1 hour at room temperature and kept for 24 hours at room temperature. The silica gel is then filtered off with suction through a glass frit (G4), stirred 3 times for 30 minutes with 500 ml of dioxane each time and sucked dry well in between. The silica gel modified by methacryloyl groups is dried at room temperature in vacuo at ~0.005 atm.

Yield: 24.8 g

Elemental analysis: C: 9.2%, H: 1.7%

Values for the silica gel modified with diol groups: C: 7.7%, H: 1.5% b) 3 g of the silica gel modified with methacryloyl groups, whose preparation is described under a), 6.0 g of optically active N-(meth)acryloyl amino acid derivative and 60 mg of azobisisobutyronitrile are dissolved or suspended in 25 ml of dry toluene in a 100 ml round-bottomed flask provided with a reflux condenser and magnetic stirrer. The apparatus is freed from air by alternately evacuating and filling with nitrogen three times and is then filled with nitrogen. The polymerization mixture is stirred for 1 hour at room temperature and then heated rapidly to 80° C. After stirring for 45 minutes at 80° C., 200 mg of 2,6-di-tert.-butyl-4-methylphenol are added and the reaction mixture is rapidly cooled. The silica gel is filtered off with suction through a glass frit (G4), washed with toluene and stirred twice with 50 ml of chloroform each time, once with 50 ml of toluene and once with 50 ml of isopropanol for 30 minutes each and filtered off with suction in between. The silica gel is taken dried at room temperature in vacuo at ~0.005 atm. The N-(meth)acryloyl amino acid derivatives polymerized onto the modified silica gel, the yields of silica gel containing optically active compounds, its nitrogen content and its content of bound polymer are compiled in Tables III and IIIa below.

c) 3.0 g of optically active N-(meth)acryloyl amino acid derivative are dissolved in chloroform (50–250 ml). 3.0 g of the silica gel modified with methacryloyl groups as in 2a) are added to this solution and the chloroform is completely removed on a rotary evaporator at a bath temperature of 40° C. 60 mg of azobisisobutyronitrile are dissolved in 30 ml of methylene chloride and added to the mixture of silica gel and monomer. The methylene chloride is removed at 30° C. and 0.02 atm and the apparatus is then made oxygen-free and filled with nitrogen. The mixture is heated to 100° C. for 3 hours. After cooling, it is stirred 3 times with 50 ml of DMF each time, once with 50 ml of THF and twice with 50 ml of isopropanol each time for 30 minutes each and filtered off with suction in between.

Drying is carried out as in method 2b). The optically active silica gels prepared as in procedure 2c) are identified in Table IIIa with an *.

TABLE III

| Example No. | N-(meth)acryloyl amino acid derivative as in Example | Yield [g] | [N content] [%] | Content of silica gel-bound polymer [weight-%] |
| --- | --- | --- | --- | --- |
| 50 | 1 | 3.2 | 0.55 | 11.1 |
| 51 | 2 | 3.3 | 0.65 | 13.1 |
| 52 | 3 | 3.1 | 0.55 | 11.1 |
| 53 | 4 | 3.4 | 0.7 | 14.8 |
| 54 | 5 | 3.35 | 1.2 | 26.6 |
| 55 | 6 | 3.45 | 0.9 | 19.9 |
| 56 | 7 | 3.3 | 0.7 | 15.5 |
| 57 | 9 | 3.2 | 0.6 | 13.8 |
| 58 | 10 | 3.35 | 0.7 | 17.2 |
| 59 | 11 | 3.0 | 0.45 | 11.1 |
| 60 | 12 | 3.15 | 0.4 | 10.2 |
| 61 | 13 | 3.2 | 0.7 | 14.8 |
| 62 | 14 | 3.25 | 0.85 | 16.9 |
| 63 | 15 | 3.1 | 0.4 | 10.2 |
| 64 | 16 | 3.2 | 0.4 | 13.6 |
| 65 | 17 | 3.4 | 1.25 | 13.8 |
| 66 | 18 | 3.3 | 1.0 | 18.2 |
| 67 | 19 | 3.5 | 0.9 | 16.8 |
| 68 | 20 | 3.2 | 0.7 | 14.5 |
| 69 | 21 | 3.7 | 1.4 | 17.8 |
| 70 | 22 | 3.1 | 0.75 | 16.1 |
| 71 | 26 | 3.1 | 0.8 | 15.9 |
| 72 | 29 | 3.5 | 0.8 | 17.7 |
| c | I a | 3.4 | 0.9 | 16.8 |
| d | I b | 3.3 | 0.8 | 13.6 |

III. Use of the optically active polymers of N-(meth)acryloyl amino acid derivatives as adsorbents for racemate separation The following test racemates were used for the chromatographic separations:

Racemate No. 1: 3-(4-chlorophenylsulphonamido)-9-(2-carboxyethyl)-1,2,3,4-tetrahydrocarbazole Racemate No. 2: 3-r-(benzenesulphonamido)-9-(2-carboxyethyl)-1,2,3,4,4a,9a-hexahydrocarbazole Racemate No. 3; 1-(carboxymethyl)-6-fluoro-9-(4-chlorobenzyl)-1,2,3,4-tetrahydrocarbazole Racemate No. 4: 2-(4-chlorophenyl)-3-methoxyimino-3-methyl-1-(1-(1,2,4-triazolyl)-2-butanol Racemate No. 5: (E)-6α[3-(4-fluorophenyl)-1-(1-methylethyl)-1H-indol-2-yl]ethenyl]tetrahydro-4β-hydroxy-2H-pyran-2-one Racemate No. 6: (E)-6α[2-(3,5-dichloro-4'-fluoro(1,1'-biphenyl]-2-yl)ethenyl]tetrahydro-4β-hydroxy-2H-pyran-2-one and Racemate No. 7: 2-(4-isobutylphenyl)-propionic acid.

The results obtained in the chromatographic separation of the different test racemates 1 to 4 with the aid of the adsorbents according to the invention (enantioselectivity α and capacity ratio $k'_1$) and the eluents used are compiled in the following Table IV.

The bead polymers were employed in a glass column (internal diameter: 1.2 cm; bed height: 30–32 cm). The column was eluted with a toluene-tetrahydrofuran (2:1) mixture (eluent a) or a toluene-dioxane (11:1) mixture (eluent b); the eluent flow rates were 0.5 ml/min with both eluents.

TABLE IV

| Example No. | Adsorbent as in Example | Test racemate | Enantio-selectivity α | Capacity ratio $k'_1$ | Eluent |
|---|---|---|---|---|---|
| 73 | 30 | 1 | 1.33 | 1.43 | a |
|  |  | 2 | 1.84 | 0.84 | a |
|  |  | 4 | 1.23 | 0.62 | b |
| 74 | 38 | 1 | 1.36 | 0.41 | a |
| 75 | 39 | 1 | 1.71 | 0.40 | a |
| 76 | 41 | 1 | 1.78 | 1.73 | a |
|  |  | 2 | 2.42 | 0.69 | a |
| 77 | 44 | 1 | 1.61 | 1.75 | a |
| 78 | 45 | 1 | 1.43 | 1.00 | a |
| 79 | 50 | 2 | 1.38 | 2.62 | c |
|  |  | 3 | 1.18 | 1.43 | c |
| 80 | 62 | 1 | 1.72 | 2.76 | c |
|  |  | 2 | 1.40 | 2.00 | c |
| 81 | 66 | 1 | 1.40 | 2.88 | c |
|  |  | 2 | 2.71 | 1.16 | c |
|  |  | 3 | 1.35 | 0.93 | c |
| 82 | 67 | 1 | 1.25 | 3.04 | c |
|  |  | 2 | 1.68 | 1.58 | c |
| 83 | 68 | 2 | 1.37 | 3.05 | c |
| 84 | 69 | 1 | 1.18 | 2.41 | c |
| 85 | 71 | 1 | 1.51 | 4.42 | c |
|  |  | 2 | 1.36 | 3.19 | c |
| 86 | 130 | 5 | 1.57 | 5.70 | d |
|  |  | 6 | 1.49 | 5.45 | d |
| 87 | 130 | 7 | 1.26 | 6.62 | e |
| 88 | 173 | 1 | 2,07 | 2,17 | g |
| 89 | 176 | 1 | 1,23 | 1,20 | f |
|  |  | 7 | 1,20 | 2,55 | c |
| 90 | 178 | 5 | 1,86 | 0,45 | h |
|  |  | 6 | 2,17 | 0,41 | h |
| 91 | 179 | 7 | 1,11 | 1,01 | c |
| 92 | 180 | 1 | 1,40 | 1,40 | g |
|  |  | 7 | 1,19 | 0,32 | c |
| 93 | 181 | 2 | 1,75 | 4,43 | g |
|  |  | 7 | 1,17 | 0,55 | c |
| 94 | 182 | 1 | 1,13 | 4,97 | f |
|  |  | 7 | 1,05 | 1,21 | c |
| 95 | 183 | 2 | 2,39 | 0,48 | g |
| 96 | 184 | 2 | 7,19 | 0,37 | g |
| 97 | 185 | 1 | 1,50 | 1,44 | g |
| 98 | 187 | 1 | 1,38 | 1,73 | g |

TABLE Ia

| Example | Optically active amino acid derivative used | N-(meth)acryloyl amino acid derivative obtained | m.p.[°C.] | $[α]_D$ (c = 1, CHCl₃) | Yield (% of theory) |
|---|---|---|---|---|---|
| 99 | L-alanine-t-butylester | N-Mea-L-alanine-t-butylester | Kp.(0.6)102 | +37.4 | 90 |
| 100 | L-alanine(+)-fenchylester | N-Mea-L-alanine-(+)-fenchylester | Oil | +8.8 | 71 |
| 101 | D-alanine-l-bornylester | N-A-D-alanine-l-bornylester | Oil | −23.0 | 60 |
| 102 | L-alanine-S-phenethylamide | N-A-L-alanine-S-phenethylamide | 157 | −160.4 | 62 |
| 103 | L-alanine-R-phenethylamide | N-A-L-alanine-R-phenylethylamide | 170 | −60.5 | 66 |
| 104 | L-valine-t-butylester | N-Mea-L-valine-t-butylester | Oil | +58.9 | 89 |
| 105 | L-alanine-l-menthylamide | N-A-L-alanine-l-menthylamide | 196 | −153.1 | 63 |
| 106 | L-alanine-l-menthylamide | N-Mea-L-alanine-l-menthylamide | 162 | −115.6 | 70 |
| 107 | L-valine-t-butylamide | N-Mea-L-valine-t-butylamide | 223 | +4.5 | 50 |
| 108 | L-leucine -l-bornylester | N-Mea-L-leucine-l-bornylester | 100 | −26.3 | 72 |
| 109 | L-leucine -l-bornylester | N-A-L-leucine-l-bornylester | 105 | −106.9 | 68 |
| 110 | L-isoleucine-l-bornylester | N-A-L-isoleucine-l-bornylester | Oil | −5.3 | 55 |
| 111 | L-phenylalanine-d-menthyl-amide | N-A-L-phenylalanine-d-menthyl-amide | 214 | +7.2 | 75 |
| 112 | L-phenylalanine-l-menthyl-amide | N-A-L-phenylalanine-l-menthyl-amide | 192 | −31.2 | 60 |
| 113 | L-phenylalanine-R-phenethyl-amide | N-A-L-phenylalanine-R-phenethyl-amide | 180 | −7.5 | 69 |
| 114 | L-leucine-d-menthylamide | N-A-L-leucine-d-menthylamide | 243 | −23.6(EtOH) | 65 |
| 115 | L-leucine-l-menthylamide | N-A-L-leucine-l-menthylamide | 208 | −134.6(EtOH) | 70 |
| 116 | L-isoleucine-l-bornylester | N-Mea-L-isoleucine-l-bornylester | 105 | −106.9 | 71 |
| 117 | L-phenylalanine-piperidide | N-A-L-phenylalanine-piperidide |  |  | 64 |
| 118 | L-proline-l-menthylamide | N-A-L-proline-l-menthylamide | 139 | −237.9 | 73 |
| 119 | L-phenylalanine-phenylester | N-A-L-phenylalanine-phenylester | 122 | +34.1 | 60 |
| 120 | L-Leucin-anilid | N-Mea-L-Leucin-anilid | 175 | −36.6 | 73 |
| 121 | L-Leucin-(2,4-dimethyl)-3-pentylester | N-Mea-L-Leucin-(2,4-dimethyl)-3-pentylester | Öl | +4.2 | 60 |
| 122 | L-Leucin-3-pentylester | N-Mea-L-Leucin-3-pentylester | Öl | +5.1 | 71 |
| 123 | L-Valin-3-pentylamid | N-Mea-L-Valin-3-pentylamid | 183 | −58.0 | 77 |
| 124 | L-Phenylalanin-cyclododecyl-ester | N-A-L-Phenylalanin-cyclo-dodecylester | 76 | +57.6 | 58 |
| 125 | L-Phenylalanin-3,5-dimethylpiperidid | N-A-L-Phenylalanin-3,5-dimethylpiperidid | Öl | −2.4 | 63 |
| 126 | L-Isoleucin-d-menthylamid | N-Mea-L-Isoleucin-d-menthylamid | 214 | +21.2 | 72 |
| 127 | L-Leucin-R-2-octylester | N-Mea-L-Leucin-R-2-octylester | Öl | −2.0 | 65 |
| 128 | L-Phenylalanin-d-neomenthyl- | N-A-L-Phenylalanin-d-neomenthyl- | 208 | −9.0 | 80 |

TABLE Ia-continued

| Example | Optically active amino acid derivative used | N-(meth)acryloyl amino acid derivative obtained | m.p.[°C.] | $[\alpha]_D$ (c = 1, CHCl$_3$) | Yield (% of theory) |
|---|---|---|---|---|---|
| | amid | amid | | | |
| 129 | L-Tryptophan-d-menthylamid | N-Mea-L-Tryptophan-d-menthylamid | 97 | +21.6 | 76 |
| 130 | L-Norleucin-l-menthylamid | N-Mea-L-Norleucin-l-menthylamid | 169 | −84.2 | 71 |
| 131 | L-Leucin-exo-norbornylamid | N-Mea-L-Leucin-exo-norbornylamid | 210 | −41.4 | 73 |
| 132 | L-Leucin-(3,3-dimethyl)-2-butylamid | N-Mea-L-Leucin-(3,3-dimethyl)-2-butylamid | 185 | | 70 |
| 133 | L-Homophenylalanin-l-menthylamid | N-Mea-L-Homophenylalanin-l-menthylamid | 147 | | 82 |
| 134 | L-Leucin-3,5-dimethylanilid | N-Mea-L-Leuin-3,5-dimethylanilid | 168 | | 71 |
| 135 | O-Benzyl-L-serin-l-menthyl-amid | N-Mea-O-Benzyl-L-serin-l-menthylamid | 95 | −6.5 | 60 |
| 136 | L-Valin-cyclohexylamid | N-Mea-L-Valin-cyclohexylamid | 181 | −35.1 | 67 |
| 137 | L-Valin-4-heptylamid | N-Mea-L-Valin-4-heptylamid | 146 | | 65 |
| 138 | L-Leucin-5-monylamid | N-Mea-L-Leucin-5-monylamid | 132 | | 68 |
| 139 | L-Leucin-stearylamid | N-Mea-L-Leucin-stearylamid | 65 | | 83 |
| 140 | L-Phenylalanin-5-nonylester | N-Mea-L-Phenylalanin-5-nonylester | Öl | −1.0 | 62 |
| 141 | L-Alanin-2-(3,3-dimethyl)-butylamid | N-Mea-L-alanin-2-(3,3-dimethyl)-butylamid | 120 | | 70 |
| 142 | L-Leucin-2-(1,3-dimethoxy)-propylamid | N-Mea-L-Leucin-2-(1,3-dimethoxy)-propylamid | 130 | −30.2 | 65 |

N-A = N-acryloyl
N-Mea = N-methacryloyl

TABLE IIa

| Example No. | N-(meth)acryloyl amino acid derivative as in Example | Rate of stirring [rpm] | Yield of beads > 10 μm [g] | Particle size of the beads [μm] | $V_s$ [ml/g] | $V_q$ [ml/g] |
|---|---|---|---|---|---|---|
| 143 | 89 | 450 | 10.8 | 25–90 | 1.7 | 5.7 |
| 144 | 94 | 450 | 10.4 | 20–70 | 2.0 | 3.5 |
| 145 | 95 | 450 | 11.1 | 20–100 | 2.2 | 5.5* |
| 146 | 97 | 450 | 11.4 | 25–110 | 2.0 | 6.9* |
| 147 | 98 | 450 | 10.8 | 20–90 | 1.6 | 5.1* |
| 148 | 99 | 450 | 9.2 | 20–100 | 1.9 | 7.0* |
| 149 | 101 | 450 | 9.5 | 15–60 | 1.9 | 8.7* |
| 150 | 105 | 450 | 9.8 | 20–90 | 2.0 | 7.9* |
| 151 | 140 | 450 | 10.2 | 10–50 | 1.8 | 7.2 |
| 152 | 141 | 450 | 13.6 | 10–60 | 2.0 | 5.8 |
| 153 | 142 | 450 | 10.5 | 15–60 | 1.6 | 8.0 |
| 154 | 144 | **400 | 10.2 | 10–100 | 2.2 | 6.8 |
| 155 | 145 | 450 | 11.7 | 15–70 | 2.1 | 7.0 |
| 156 | 146 | ***450 | 12.6 | 10–45 | 1.8 | 6.3 |
| 157 | 148 | ****400 | 12.0 | 15–60 | 2.0 | 5.6 |
| 158 | 149 | 400 | 12.8 | 15–80 | 1.6 | 4.4 |
| 159 | 158 | 450 | 11.3 | 20–100 | 1.9 | 5.9 |

*Swelling agent: Toluene-Tetrahydrofuran 3:2
**12,5 g Methacryloyl acid derivative + 2,5 g Ethylenglykoldimethacrylat
***13,5 g Methacryloyl acid derivative + 1,5 g N,N'-Diacryloylpiperazin
****13,5 g Methacryloyl acid derivative + 1,5 g Divinylbenzol (77% ig)

TABLE IIIa

| Example No. | N-(meth)acryloyl amino acid derivative as in Example | Yield [g] | [N content] [%] | Content of silica gel bound polymer [weight-%] |
|---|---|---|---|---|
| 160 | 88 | 3.05 | 1.0 | 15.2 |
| 161 | 89 | 3.2 | 0.9 | 18.0 |
| 162 | 90 | 3.5 | 0.8 | 16.0 |
| 163 | 91 | 3.1 | 1.7 | 15.0 |
| 164* | 92 | 4.1 | 3.9 | 34.2 |
| 165 | 93 | 3.2 | 0.9 | 15.5 |
| 166 | 94 | 3.5 | 1.8 | 18 |
| 167 | 95 | 3.1 | 1.3 | 13.7 |
| 168* | 96 | 3.3 | 1.5 | 12.1 |
| 169 | 97 | 3.2 | 0.6 | 14.4 |
| 170 | 98 | 3.0 | 0.7 | 16.1 |
| 171 | 99 | 3.0 | 0.7 | 16.1 |
| 172* | 100 | 3.6 | 1.5 | 19.1 |
| 173 | 101 | 3.1 | 1.1 | 14.0 |
| 174 | 102 | 3.4 | 1.6 | 18.4 |
| 175* | 103 | 3.1 | 1.5 | 17.3 |
| 176* | 104 | 3.3 | 2.0 | 23.0 |
| 177 | 105 | 3.0 | 0.6 | 14.4 |
| 178 | 106 | 3.2 | 1.6 | 16.4 |
| 179 | 107 | 3.1 | 1.4 | 15.3 |
| 180 | 108 | 3.2 | 0.8 | 16.9 |
| 181 | 138 | 3.2 | 1.15 | 11.3 |
| 182 | 139 | 3.3 | 0.6 | 12.7 |
| 183 | 140 | 3.35 | 0.8 | 15.4 |
| 184 | 141 | 3.15 | 2.0 | 18.2 |
| 185 | 142 | 3.3 | 0.5 | 13.8 |
| 186 | 143 | 3.4 | 1.4 | 15.7 |
| 187 | 144 | 3.2 | 1.15 | 13.8 |
| 188 | 145 | 3.15 | 0.3 | 6.7 |
| 189 | 146 | 3.3 | 1.1 | 14.0 |
| 190 | 147 | 3.3 | 1.4 | 13.7 |
| 191 | 148 | 3.2 | 0.8 | 9.6 |
| 192 | 149 | 3.3 | 1.3 | 13.6 |
| 193 | 151 | 3.3 | 0.9 | 12.1 |
| 194 | 152 | 3.1 | 0.75 | 8.1 |
| 195 | 153 | 3.3 | 1.1 | 15.7 |

TABLE IIIa-continued

| Example No. | N-(meth)acryloyl amino acid derivative as in Example | Yield [g] | [N content] [%] | Content of silica gel bound polymer [weight-%] |
|---|---|---|---|---|
| 196 | 154 | 3.2 | 1.3 | 13.0 |
| 197 | 158 | 3.1 | 0.5 | 12.3 |
| 198 | 159 | 3.0 | 1.9 | 16.3 |
| 199 | 160 | 3.4 | 1.95 | 20.9 |

It is understood that the specification and examples are illustrative but not limitative of the present invention and that other embodiments within the spirit and scope of the invention will suggest themselves to those skilled in the art.

We claim:

1. An optically active N-(meth)acryloyl amino acid amide of the formula

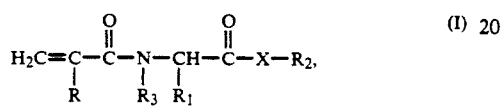

(I)

in which

R is hydrogen or methyl, $R_1$ represents alkyl with 1 to 18 carbon atoms or cycloalkyl with 3 to 8 carbon atoms which are optionally substituted by hydroxy, halogen, alkoxy or cycloalkyl with up to 8 carbon atoms or by an aryl group with 4 to 14 carbon atoms or by a heteroaryl group which contains 1 or 2 hetero atoms selected from the group consisting of nitrogen, oxygen and sulphur, which aryl- and heteroaryl groups are optionally substituted by hydroxy, halogen, alkyl or alkoxy with 1 to 4 carbon atoms each, $R_3$ represents hydrogen or denotes together with $R_1$ a tri- or tetramethylene group, X denotes oxygen or the group $NR_4$ wherein $R_4$ represents hydrogen or alkyl with 1 to 4 carbon atoms or $R_4$ builds together with $R_2$ and the nitrogen atom a 5- to 7-membered heterocyclic ring which ring may optionally be substituted by the group COO-alkyl (1–4 carbon atoms) or by one or two alkyl radicals (1–4 carbon atoms) and $R_2$ denotes a strongly space-filling hydrocarbon radical with up to 30 carbon atoms selected from the group consisting of highly branched-alkyl with 4 to 20 carbon atoms, $CH_2$-highly branched alkyl with 4 to 20 carbon atoms, cycloalkyl with 3 to 10 carbon atoms and aryl with 4 to 14 carbon atoms, which forementioned alkyl-, cycloalkyl- and arylgroups are optionally substituted by halogen, hydroxy, alkyl with 1 to 8 carbon atoms and/or alkoxy with 1 to 8 carbon atoms, or $R_2$ denotes terpenyl, adamantyl or decahydro-naphthyl, with the proviso that if $R_2$ is a tertiary butyl group or X is $NR_2$, R must be a methyl group.

2. An amide according to claim 1 of an optically active amino acid selected from the group alaline, aminobutyric acid, valine, norvaline, leucine, isoleucine, terleucine, phenylglycine, phenylalanine, naphthylalanine, cyclohexylglycine, cyclohexylalanine, tyrosine, tryptophan, threonine, serine, aspartic acid, glutamic acid, ornithine, lysine and proline.

3. A compound according to claim 1, wherein such compound is N-acryloyl-L-alanine d-menthyl ester.

4. A compound according to claim 1, wherein such compound is N-acryloyl-L-phenylalanine d-menthyl ester.

5. A compound according to claim 1, wherein such compound is N-acryloyl-L-alanine (+)-fenchyl ester.

6. A compound according to claim 1, wherein such compound is N-methacryloyl-L-leucine tert.-butyl ester.

7. A compound according to claim 1, wherein such compound is N-methacryloyl-L-phenylalanine-1-menthylamide.

8. An optically active poly(meth)acrylamide containing structural units of the formula (IV)

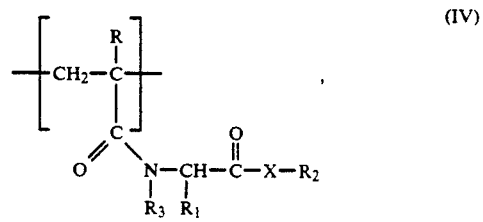

(IV)

in which

R is hydrogen or methyl, $R_1$ represents alkyl with 1 to 18 carbon atoms or cycloalkyl with 3 to 8 carbon atoms which are optionally substituted by hydroxy, halogen, alkoxy or cycloalkyl with up to 8 carbon atoms or by an aryl group with 4 to 14 carbon atoms or by a heteroaryl group which contains 1 or 2 hetero atoms selected from the group consisting of nitrogen, oxygen and sulphur, which aryl- and heteroaryl groups are optionally substituted by hydroxy, halogen, alkyl or alkoxy with 1 to 4 carbon atoms each, $R_3$ represents hydrogen or denotes together with $R_1$ a tri- or tetramethylene group, X denotes oxygen or the group $NH_4$ wherein $R_4$ represents hydrogen, or alkyl with 1 to 4 carbon atoms or $R_4$ builds together with $R_2$ and the nitrogen atom a 5- to 7-membered heterocyclic ring which ring may optionally be substituted by the group COO-alkyl (1–4 carbon atoms) or by one or two alkyl radicals (1–4 carbon atoms) and $R_2$ denotes a strongly space-filling hydrocarbon radical with up to 30 carbon atoms selected from the group consisting of highly branched-alkyl with 4 to 20 carbon atoms, $CH_2$-highly branched alkyl with 4 to 20 carbon atoms, cycloalkyl with 3 to 10 carbon atoms and aryl with 4 to 14 carbon atoms, which forementioned alkyl-, cycloalkyl- and arylgroups are optionally substituted by halogen, hydroxy, alkyl with 1 to 8 carbon atoms and/or alkoxy with 1 to 8 carbon atoms, or $R_2$ denotes terpenyl, adamantyl or decahydronaphthyl, with the proviso that if $R_2$ is a tertiary butyl group or X is $NR_2$, R must be a methyl group.

9. An optically active poly(meth)acrylamide according to claim 8, in the form of a cross-linked or linear polymer.

10. An optically active poly(meth)acrylamide according to claim 8 bound to a finely divided inorganic support material.

11. In the chromatographic separation of a component of a racemic mixture by contact with an optically active poly(meth)acrylamide, the improvement wherein said poly(meth)acrylamide is a poly(meth)acrylamide according to claim 8.

* * * * *

UNITED STATES PATENT AND TRADEMARK OFFICE
CERTIFICATE OF CORRECTION

PATENT NO. : 5,274,167
DATED : December 28, 1993
INVENTOR(S) : Lange, et al.

It is certified that error appears in the above-indentified patent and that said Letters Patent is hereby corrected as shown below:

| | |
|---|---|
| Title Page & Col. 1 | Item [54]: Line 1 delete " POLYMERIABLE " and substitute -- POLYMERIZABLE -- |
| Title Page | Foreign Application Priority Data: Delete " Jan. 26, 1989 [JP] Japan... 1-11972 " |
| Col. 18, line 37 | Delete " $NH_4$ " and substitute -- $NR_4$ -- |

Signed and Sealed this

Twenty-fifth Day of February, 1997

Attest:

BRUCE LEHMAN

*Attesting Officer*  *Commissioner of Patents and Trademarks*